(12) United States Patent
Yonemura

(10) Patent No.: US 8,396,675 B2
(45) Date of Patent: Mar. 12, 2013

(54) METHOD AND APPARATUS FOR DETERMINING DISCHARGE FLOW RATE AND USE OF THE APPARATUS

(75) Inventor: Masao Yonemura, Akashi (JP)

(73) Assignee: TLV Co., Ltd., Hyogo (JP)

(\*) Notice: Subject to any disclaimer, the term of this patent is extended or adjusted under 35 U.S.C. 154(b) by 297 days.

(21) Appl. No.: 12/746,062

(22) PCT Filed: Jan. 26, 2010

(86) PCT No.: PCT/JP2010/050929
§ 371 (c)(1),
(2), (4) Date: Aug. 23, 2010

(87) PCT Pub. No.: WO2010/098161
PCT Pub. Date: Sep. 2, 2010

(65) Prior Publication Data
US 2011/0054812 A1 Mar. 3, 2011

(30) Foreign Application Priority Data
Feb. 26, 2009 (JP) .................................. 2009-044439

(51) Int. Cl.
 *G01F 1/66* (2006.01)
 *G06F 19/00* (2011.01)
 *G01M 3/24* (2006.01)
(52) U.S. Cl. .......................... 702/48; 73/861.27; 702/51
(58) Field of Classification Search .................. 702/39, 702/47, 48, 50, 51, 97, 98, 100, 103, 138, 702/150, 151, 158; 73/40.5 A, 644, 861.29; 700/283, 284
See application file for complete search history.

(56) References Cited

U.S. PATENT DOCUMENTS

| 5,719,785 | A | 2/1998 | Standifer |
| 6,070,468 | A * | 6/2000 | Degertekin et al. ............. 73/644 |
| 6,247,353 | B1 | 6/2001 | Battenberg et al. |

FOREIGN PATENT DOCUMENTS

| JP | 58-48817 A | 3/1983 |
| JP | 60-87870 A | 5/1985 |
| JP | 5-142010 A | 6/1993 |
| JP | 755624 A | 3/1995 |
| JP | 7-253376 A | 10/1995 |
| JP | 2002-90253 A | 3/2002 |
| JP | 2004-317191 A | 11/2004 |
| JP | 2005-300175 A | 10/2005 |
| JP | 2006266767 A | 10/2006 |

\* cited by examiner

*Primary Examiner* — John H Le
(74) *Attorney, Agent, or Firm* — The Webb Law Firm

(57) ABSTRACT

The object is to facilitate determination of a flow rate of fluid discharged from a discharge opening.
Intensity of a supersonic wave generated at and propagated from a discharge opening in association with discharge of the fluid from the discharge opening is determined at a determinate site distant from the discharge opening. And, a propagation distance from the discharge opening to the determination site is determined or investigated. Then, based upon a correlation existent among the intensity of the propagated supersonic wave, the propagation distance and the fluid discharge flow rate from the discharge opening, the fluid discharge rate is obtained from the determined or investigated supersonic wave intensity and the propagation distance.

10 Claims, 2 Drawing Sheets

METHOD AND APPARATUS FOR DETERMINING DISCHARGE FLOW RATE AND USE OF THE APPARATUS

TECHNICAL FIELD

The present invention relates to a method and an apparatus for determining a discharge flow rate of fluid discharged from a discharge opening formed at a terminal end of a discharge passageway installed in a factory or the like that discharges or emits various kinds of fluid. The invention relates also to use of such discharge flow rate determining apparatus.

BACKGROUND ART

As flowmeters, various types are known. Many of them are configured to be incorporated in midway a pipe passageway (see Patent Document 1). These known flowmeters suffer the problem that the flowmeter when incorporated acts as a passageway resistance, thus resulting in significant pressure loss of the transported fluid. Another problem thereof is the need to stop the fluid transport in order to incorporate the flowmeter in an existing pipe passageway. They suffer a still further problem of inability to be readily moved to a site where a flow rate determination is needed.

Further, some flowmeters are capable of effecting flow rate determination from the outside of the pipe passageway, as is the case with e.g. a supersonic wave flowmeter utilizing the ultrasonic propagation period or the Doppler effect (see Patent Document 2). With this too, an apparatus or the like needs to be mounted to a pipe passageway, so there is the problem of its mounting requiring significant trouble. In particular, if the site to be determined is located at a hardly accessible location such as a high site, the mounting operation requires great trouble and mounting cost.

PRIOR ART DOCUMENTS

Patent Documents
Patent Document 1: Japanese Patent Application "Kokai" No. 5-142010
Patent Document 2: Japanese Patent Application "Kokai" No. 58-48817

SUMMARY OF THE INVENTION

Problem to be Solved by Invention

In view of the above-described state of the art, the principal object of the present invention is to provide a method and an apparatus for determining discharge flow rate, which method and apparatus allow extremely easy determination, from the outside, of a flow rate of a fluid discharged from a discharge opening formed at a terminal end of a discharge passageway, without being restricted by the position of the discharge opening and also to provide use of such discharge flow rate determining apparatus which use can enhance the usefulness of this discharge flow determining apparatus.

Means to Achieve Object

The first characterizing feature of the present invention relates to a method for determining a discharge flow rate, according to which:

A method for determining a flow rate of a fluid discharged from a discharge opening formed at a terminal end of a discharge passageway, the method comprising the steps of:

determining intensity of a supersonic wave generated at and propagated from the discharge opening in association with discharge of the fluid from the discharge opening, at a determination site distant from the discharge opening; and determining the discharge flow rate of the fluid from the discharge opening from the determined supersonic wave intensity, based on a correlation existent between the intensity of the supersonic wave at the determination site and the discharge flow rate of the fluid from the discharge opening.

As a result of study on a flow rate of a fluid discharged from a discharge opening at a terminal end of a discharge passageway, a certain correlation was found between the fluid discharge flow rate from the discharge opening and the intensity of supersonic wave generated at and propagated from the discharge opening in association with that discharge of the fluid. Qualitatively, the greater the flow rate of the discharged fluid, the higher the intensity of the supersonic wave.

Therefore, if the correlation existing between the intensity of supersonic wave determined at the determination site distant from the discharge opening and the discharge flow rate of the fluid is obtained experimentally, the discharge flow rate of the fluid from the discharge opening can be obtained from thus determined supersonic wave intensity, based on such correlation.

That is to say, with this determining method, the determination of the discharge flow rate of fluid from the discharge opening is possible without the need for incorporating or mounting of an apparatus or equipment in/to the discharge passageway. Therefore, even in case the discharge opening is located at a hardly accessible location such as a high location, the discharge flow rate of the fluid from the discharge opening can be determined easily. Further, it is also possible to avoid such inconveniences as the increase of pressure loss in the transported fluid due to the presence of the apparatus or equipment incorporated in midway a discharge passageway.

Further, due to the no need for mounting of the apparatus to the discharge passageway, the determining apparatus or the like can be provided as a readily portable type. Therefore, such mode of determination where the apparatus is moved as needed to different places to be determined to effect the fluid discharge flow rate determination can be realized easily.

Moreover, as this method comprises a flow rate determination based on determination of supersonic wave intensity, the method is less affected by the temperature of the fluid discharged from the discharge opening. Therefore, even when the discharged fluid from the discharge opening is a hot fluid, the discharge flow rate of this fluid from the discharge opening can be determined accurately and easily.

The second characterizing feature of the present invention relates to a method for determining a discharge flow rate, according to which:

A method for determining a flow rate of a fluid discharged from a discharge opening formed at a terminal end of a discharge passageway, the method comprising the steps of:

determining intensity of a supersonic wave generated at and propagated from the discharge opening in association with discharge of the fluid from the discharge opening, at a determination site distant from the discharge opening;

determining or investigating a propagation distance from the discharge opening to the determination site; and determining the discharge flow rate of the fluid from the discharge opening from the determined supersonic wave intensity and the propagation distance, based on a correlation existent among the intensity of the supersonic wave at the determination site, the propagation distance and the flow rate of the fluid discharged from the discharge opening.

That is, with this determining method, with respect to the portions thereof common to the determining method according to the first characterizing feature, basically same advantageous effects can be achieved.

In addition, with this determining method, from the supersonic wave intensity determined at the determination site and the determined or investigated propagation distance, and based upon the correlation existent among the supersonic wave intensity, the propagation distance and the fluid discharge flow rate, the flow rate of the fluid discharged from the discharge opening is determined. Therefore, this method is capable of readily effecting the fluid discharge flow rate determination, with flexibly coping with any difference in the propagation distance from the discharge opening to the determination site.

Namely, even if the propagation distance from the discharge opening to the determination site (in other words, the distance between the discharge opening and the determination site) varies in many ways, regardless of such propagation distance variations, the determination of the fluid discharge flow rate can be effected accurately and easily. In this respect, the discharge flow rate determining method can be even superior in the respects of general versatility and convenience.

And, with the above-described ability of flexibly coping with propagation distance variations, such mode of determination where the apparatus is moved as needed to different places to be determined to effect the fluid discharge flow rate determination can be realized even more easily and effectively.

Incidentally, although the propagation distance can be determined or investigated by any known method, in case the discharge opening is located at a hardly accessible place, its determination may use a distance metering instrument of the type determining the distance to the discharge opening, with its determining end being directed toward the discharge opening. Further, this investigation may be made with using a piping diagram of the system of interest. Or, in some cases, the determination may be a visual determination or estimation.

The third characterizing feature of the present invention relates to a method for determining a discharge flow rate, according to which:

A method for determining a flow rate of a fluid discharged from a discharge opening formed at a terminal end of a discharge passageway, the method comprising the steps of:

determining intensity of a supersonic wave generated at and propagated from the discharge opening in association with discharge of the fluid from the discharge opening, at a determination site distant from the discharge opening;

determining or investigating a propagation angle formed by the propagation direction of the propagated supersonic wave to the determination site relative to the direction of the fluid discharge from the discharge opening; and determining the discharge flow rate of the fluid from the discharge opening from the determined supersonic wave intensity and the determined or investigated propagation angle, based on a correlation existent among the intensity of the supersonic wave at the determination site, the propagation angle and the flow rate of the fluid discharged from the discharge opening.

That is, with this determining method, with respect to the portions thereof common to the determining method according to the first characterizing feature, basically same advantageous effects can be achieved.

In addition, with this determining method, from the supersonic wave intensity determined at the determination site and the determined or investigated propagation angle, and based upon the correlation existent between the supersonic wave intensity, the propagation angle and the fluid discharge flow rate, the flow rate of the fluid discharged from the discharge opening is determined. Therefore, this method is capable of readily effecting the fluid discharge flow rate determination, with flexibly coping with any difference in the propagation angle.

Namely, even if the propagation angle formed by the propagation direction of the supersonic wave to the determination site relative to the fluid discharge direction (in other words, the intersection angle between the propagation direction of the supersonic wave to the determination site and the discharge direction of the fluid from the discharge opening) varies in many ways, regardless of such propagation angle variations, the determination of the fluid discharge flow rate can be effected accurately and easily. In this respect, the discharge flow rate determining method can be even superior in the respects of general versatility and convenience.

And, with the above-described possibility of flexibly coping with propagation angle variations, such mode of determination where the apparatus is moved as needed to different places to be determined to effect the fluid discharge flow rate determination can be realized even more easily and effectively.

Incidentally, although the propagation angle can be determined or investigated by any known method, in case the discharge opening is located at a hardly accessible place, its determination or investigation may be made with using a piping diagram of the system of interest. Or, it may use a trigonometer, an elevation angle meter or the like. Or, in some cases, the determination may be a visual determination or estimation.

The fourth characterizing feature of the present invention relates to a method for determining a discharge flow rate, according to which:

A method for determining a flow rate of a fluid discharged from a discharge opening formed at a terminal end of a discharge passageway, the method comprising the steps of:

determining intensity of a supersonic wave generated at and propagated from the discharge opening in association of discharge of the fluid from the discharge opening, at a determination site distant from the discharge opening;

determining or investigating a propagation distance from the discharge opening to the determination site and a propagation angle formed by the propagation direction of the propagated supersonic wave to the determination site relative to the direction of the fluid discharge from the discharge opening; and determining the discharge flow rate of the fluid from the discharge opening from the determined or investigated supersonic wave intensity, the propagation distance and the propagation angle, based on a correlation existent among the intensity of the supersonic wave, the propagation angle and the flow rate of the fluid discharged from the discharge opening.

That is, with this determining method, with respect to the portions thereof common to the determining method according to the first characterizing feature, basically same advantageous effects can be achieved. In addition, this method implements in combination the determining method according to the second characterizing feature and the determining method according to the third characterizing feature, so that the method is capable of flexibly coping with propagation distance variations and propagation angle variations. In this respect, the discharge flow rate determining method can be even superior in the respects of general versatility and convenience.

In implementing the determining methods according to the first through fourth characterizing features, advantageously, the respective correlations used in these determining methods may be obtained in advance by way of e.g. experiments conducted at other site(s), prior to e.g. the determination or investigation of the supersonic wave at the determination site.

The fifth characterizing feature of the present invention specifies a preferred mode of embodiment for embodying the discharge flow rate determining method according to the third or fourth characterizing feature, according to which:

the determination of the supersonic wave intensity at the determination site is effected with using a microphone for determining the supersonic intensity, with the microphone being directed toward the discharge opening; and the propagation angle is determined based on the direction of the microphone at this time of supersonic wave intensity determination and the determined or investigated direction of the fluid discharged from the discharge opening.

That is to say, with this determining method, since the propagation angle is obtained by utilizing the direction of the microphone used in determining the intensity of the propagated supersonic wave at the determination site, the number of steps and/or the number of instruments such as the metering instrument for the determination operation can be reduced. Therefore, the determination operation can be even more simplified.

The sixth characterizing feature of the present invention specifies a preferred mode of embodiment for embodying the discharge flow rate determining method according to the fourth characterizing feature, according to which:

the determination of the propagation distance is effected with using a distance meter at the determination site for determining the distance to the discharge opening, with a metering end of the distance meter being directed to the discharge opening; and the propagation angle is determined based on the direction of the metering end of the distance meter at this time of the distance determination and the determined or investigated direction of the fluid discharged from the discharge opening.

That is, with this determining method, since the propagation angle is obtained by utilizing the direction of the metering end of the distance meter at this time of the distance determination at the determination site, the number of steps and/or the number of instruments such as the metering instrument for the determination operation can be reduced. Therefore, the determination operation can be even more simplified.

The seventh characterizing feature of the present invention relates to an apparatus for determining a discharge flow rate, according to which:

An apparatus for determining a flow rate of a fluid discharged from a discharge opening formed at a terminal end of a discharge passageway, the apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent between the intensity of the supersonic wave at the determination site and the discharge flow rate of the fluid from the discharge opening;

calculating means for calculating the discharge flow rate of the fluid from the discharge opening from the supersonic wave intensity determined by the supersonic wave determining means at the determination site, based on the correlation stored in the storing means; and outputting means for outputting the discharge flow rate of the fluid from the discharge opening calculated by the calculating means as the determination result.

That is, with using this determining apparatus, by implementing the determining method according to the first characterizing feature, the above-described advantageous effect achieved by the determining method according to the first characterizing feature can be obtained.

Further, with this determining apparatus, since the calculation of the fluid discharge flow rate based on the above-described correlation is effected automatically by the calculating means, the determination of the fluid discharge flow rate form the discharge opening can be effected even more easily and efficiently.

The eighth characterizing feature of the present invention relates to an apparatus for determining a discharge flow rate, according to which:

An apparatus for determining a flow rate of a fluid discharged from a discharge opening formed at a terminal end of a discharge passageway, the apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent among the intensity of the supersonic wave, the propagation distance from the discharge opening to the determination site and the discharge flow rate of the fluid from the discharge opening;

calculating means for calculating the discharge flow rate of the fluid from the discharge opening from the supersonic wave intensity determined by the supersonic wave determining means at the determination site and the propagation distance inputted to an inputting section, based on the correlation stored in the storing means; and outputting means for outputting the discharge flow rate of the fluid from the discharge opening calculated by the calculating means as the determination result.

That is, with using this determining apparatus, by implementing the determining method according to the second characterizing feature, the above-described advantageous effect achieved by the determining method according to the second characterizing feature can be obtained.

Further, with this determining apparatus, since the calculation of the fluid discharge flow rate based on the above-described correlation is effected automatically by the calculating means, the determination of the fluid discharge flow rate form the discharge opening can be effected even more easily and efficiently.

Incidentally, like the case of the determining method according to the second characterizing feature, the propagation distance to be inputted to the inputting section can be determined or investigated by any known method, in case the discharge opening is located at a hardly accessible place, its determination may use a distance metering instrument of the type determining the distance to the discharge opening, with its determining end being directed toward the discharge opening. Further, this investigation may be made with using a piping diagram of the system of interest. Or, in some cases, the determination may be a visual determination or estimation.

Further, in case the propagation distance is determined with using a distance meter or the like, it may be arranged such that the propagation distance as the determination result is automatically inputted from the distance meter to the inputting section.

The ninth characterizing feature of the present invention relates to an apparatus for determining a discharge flow rate, according to which:

An apparatus for determining a flow rate of a fluid discharged from a discharge opening formed at a terminal end of a discharge passageway, the apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent among the intensity of the propagated supersonic wave at the determination site, a propagation angle formed by the propagation direction of the propagated supersonic wave to the determination site relative to the direction of the fluid discharge from the discharge opening and the fluid discharge flow rate from the discharge opening;

calculating means for calculating the discharge flow rate of the fluid from the discharge opening from the supersonic wave intensity determined by the supersonic wave determining means at the determination site and the propagation angle inputted to an inputting section, based on the correlation stored in the storing means; and outputting means for outputting the discharge flow rate of the fluid from the discharge opening calculated by the calculating means as the determination result.

That is, with using this determining apparatus, by implementing the determining method according to the third characterizing feature, the above-described advantageous effect achieved by the determining method according to the third characterizing feature can be obtained.

Further, with this determining apparatus, since the calculation of the fluid discharge flow rate based on the above-described correlation is effected automatically by the calculating means, the determination of the fluid discharge flow rate form the discharge opening can be effected even more easily and efficiently.

Incidentally, like the case of the determining method according to the third characterizing feature, although the propagation angle can be determined or investigated by any known method, in case the discharge opening is located at a hardly accessible place, its determination or investigation may be made with using a piping diagram of the system of interest. Or, it may use a trigonometer, an elevation angle meter or the like. Or, in some cases, the determination may be a visual determination or estimation.

Further, it may be arranged such that the propagation angle of the propagated supersonic wave to the determination site as the propagation angle equivalent information and the fluid discharge direction from the discharge opening are inputted to the inputting section and from these inputted information, the propagation angle for use in the calculation of the fluid discharge flow amount is calculated by the calculating means per se.

The tenth characterizing feature of the present invention relates to an apparatus for determining a discharge flow rate, according to which:

An apparatus for determining a flow rate of a fluid discharged from a discharge opening formed at a terminal end of a discharge passageway, the apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent among the intensity of the supersonic wave at the determination site, the propagation distance from the discharge opening to the determination site, the propagation angle formed by the propagation direction of the propagated supersonic wave to the determination site relative to the direction of the fluid discharge from the discharge opening and the fluid discharge flow rate from the discharge opening;

calculating means for calculating the discharge flow rate of the fluid from the discharge opening from the supersonic wave intensity determined by the supersonic wave determining means, the propagation distance and the propagation angle inputted to an inputting section, based on the correlation stored in the storing means; and outputting means for outputting the discharge flow rate of the fluid from the discharge opening calculated by the calculating means as the determination result.

That is, with using this determining apparatus, by implementing the determining method according to the fourth characterizing feature, the above-described advantageous effect achieved by the determining method according to the fourth characterizing feature can be obtained.

Further, with this determining apparatus, since the calculation of the fluid discharge flow rate based on the above-described correlation is effected automatically by the calculating means, the determination of the fluid discharge flow rate form the discharge opening can be effected even more easily and efficiently.

Incidentally, like the case of the determining apparatus according to the eighth characterizing feature, the propagation distance to be inputted to the inputting section can be determined or investigated by any known method, in case the discharge opening is located at a hardly accessible place, its determination may use a distance metering instrument of the type determining the distance to the discharge opening, with its determining end being directed toward the discharge opening. Further, this investigation may be made with using a piping diagram of the system of interest. Or, in some cases, the determination may be a visual determination or estimation.

Further, in case the propagation distance is determined with using a distance meter or the like, it may be arranged such that the propagation distance as the determination result is automatically inputted from the distance meter to the inputting section.

Further, like the determining apparatus according to the ninth characterizing feature, although the propagation angle to be inputted to the inputting section can be determined or investigated by any known method, in case the discharge opening is located at a hardly accessible place, its determination or investigation may be made with using a piping diagram of the system of interest. Or, it may use a trigonometer, an elevation angle meter or the like. Or, in some cases, the determination may be a visual determination or estimation.

Further, it may be arranged such that the propagation angle of the propagated supersonic wave to the determination site as the propagation angle equivalent information and the fluid discharge direction from the discharge opening are inputted to the inputting section and from these inputted information, the propagation angle for use in the calculation of the fluid discharge flow amount is calculated by the calculating means per se.

The eleventh characterizing feature of the present invention relates to a use of the discharge flow rate determining apparatus according to any one of the above-described seventh through the tenth characterizing features; according to which:

configuring the apparatus to be capable of selectively providing;

a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and a leaking portion searching mode in which intensity of the supersonic wave generated at a leaking portion in association with leakage of fluid is determined by the supersonic wave determining means while the supersonic wave determining means is being moved or changed in its posture and the leaking portion is searched based upon the determined intensity of the supersonic wave at the leaking portion; and selectively effecting the discharge flow rate determining mode and the leaking portion searching mode.

That is, with this use, when the discharge flow rate determining mode is selected, the discharge flow rate determining apparatus according to any one of the seventh through tenth characterizing features is used in the mode of use described above (i.e. the determining method according to any one of the first through sixth characterizing features is implemented), thus determining the discharge flow rate of the fluid from the discharge opening.

On the other hand, when the leaking portion searching mode is selected, the intensity of the supersonic wave generated at a leaking portion in association with leakage of fluid is determined by the supersonic wave determining means while the supersonic wave determining means is being moved or changed in its posture, so that any change in the determined supersonic wave intensity is grasped and the based on the pattern of this change, the leaking portion is searched. That is, with selection of this leaking portion searching mode, it is possible to readily discover even a small fluid leaking portion due to e.g. a pinhole generated at a pipe or a tank or connection failure at a pipe joint.

And, by selectively using the discharge flow rate determining mode originally provided and the leaking portion searching mode utilizing the determining function of the supersonic wave determining means for the different purpose, the usefulness of the discharge flow rate determining apparatus according to the seventh to tenth characterizing features can be enhanced. Therefore, the user will find the determining apparatus even more useful and convenient.

The twelfth characterizing feature of the present invention relates to a use of the discharge flow rate determining apparatus according to any one of the above-described seventh through the tenth characterizing features; according to which:

configuring the apparatus to be capable of selectively providing;

a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and a leakage flow rate determining mode in which intensity of the supersonic wave generated at a leaking portion in association with leakage of fluid is determined by the supersonic wave determining means and the calculating means is caused to calculate a fluid leakage flow rate at the leaking portion based upon the determined intensity of the supersonic wave at the leaking portion; and selectively effecting the discharge flow rate determining mode and the leaking portion searching mode.

That is, with this use, when the discharge flow rate determining mode is selected, the discharge flow rate determining apparatus according to any one of the seventh through tenth characterizing features is used in the mode of use described above (i.e. the determining method according to any one of the first through sixth characterizing features is implemented), thus determining the discharge flow rate of the fluid from the discharge opening.

On the other hand, when the leakage flow rate determining mode is selected, intensity of the supersonic wave generated at a leaking portion in association with leakage of fluid is determined by the supersonic wave determining means and the calculating means is caused to calculate a fluid leakage flow rate at the leaking portion based upon a correlation existent between intensity of the supersonic wave generated at the leaking portion and the fluid leakage flow rate at the leaking portion. That is, with selection of this leakage flow rate determining mode, it is possible to readily determine a leakage flow rate of even a small fluid leaking portion due to e.g. a pinhole generated at a pipe or a tank or connection failure at a pipe joint.

And, by selectively using the discharge flow rate determining mode originally provided and the leakage flow rate determining mode utilizing the determining function of the supersonic wave determining means for the different purpose, the usefulness of the discharge flow rate determining apparatus according to the seventh to tenth characterizing features can be enhanced. Therefore, the user will find the determining apparatus even more useful and convenient.

Incidentally, in implementing the use of apparatus according to the eleventh or twelfth characterizing feature, for enabling the selective implementation of the discharge flow rate determining mode and the leaking portion searching mode and the selective implementation of the discharge flow rate determining mode and the leakage flow rate determining mode, various arrangements for switchover for mode selection are conceivable, including, but not limited to, an arrangement of enabling change in the metering sensitivity or metering frequency range of the supersonic wave determining means, an arrangement for enabling change in the calculation program of the calculating means, and an arrangement for enabling change in the stored information in the storing means, or a change of a part of the hardware of the apparatus.

Further, in order to enable change in the calculation program or the stored information, it is possible to employ a method according to which a plurality of kinds of program or a plurality of kinds of stored information are inputted in advance to the determining apparatus so that a desired calculation program or stored information may be selected at the time of mode selection. Or, it is possible to employ a method according to which a new calculation program or stored information is inputted at the time of mode selection.

Furthermore, it is possible to employ an arrangement of enabling selective implementation of the three modes, i.e. the discharge flow rate determining mode, the leaking portion searching mode and the leakage flow rate determining mode, thus implementing the apparatus use according to the eleventh characterizing feature and the apparatus use according to the twelfth characterizing feature in combination. In this case, the usefulness and the convenience of the discharge flow rate determining apparatus can be even more enhanced.

In implementing the discharge flow rate determining method according to any one of the first through sixth characterizing features, or implementing the discharge flow rate determining apparatus according to any one of the seventh through tenth characterizing features or implementing the use of the discharge flow rate determining apparatus according to the eleventh or twelfth characterizing features, the correlations used in these implementations can take any form such as a mathematical expression form or a form of data table, etc.

Further, the determination site can be any location that can face the discharge opening. But, in case the determination can be restricted or hindered by the fluid being discharged from the discharge opening or by the construction of the discharge opening, it is desirable to locate the determination site at a location present in a direction intersecting the discharge direction of the fluid discharged from the discharge opening. And, it is particularly desirable to place at such a location present in the direction normal to the discharge direction of the fluid discharged from the discharge opening.

The fluid discharged from the discharge opening as the target of determination can be any gas, liquid or mixture of gas and liquid or mixture fluid of gas and particulate solid matter And, such gas can be moist gas or dry gas.

MODES OF EMBODYING THE INVENTION

Figure 1:
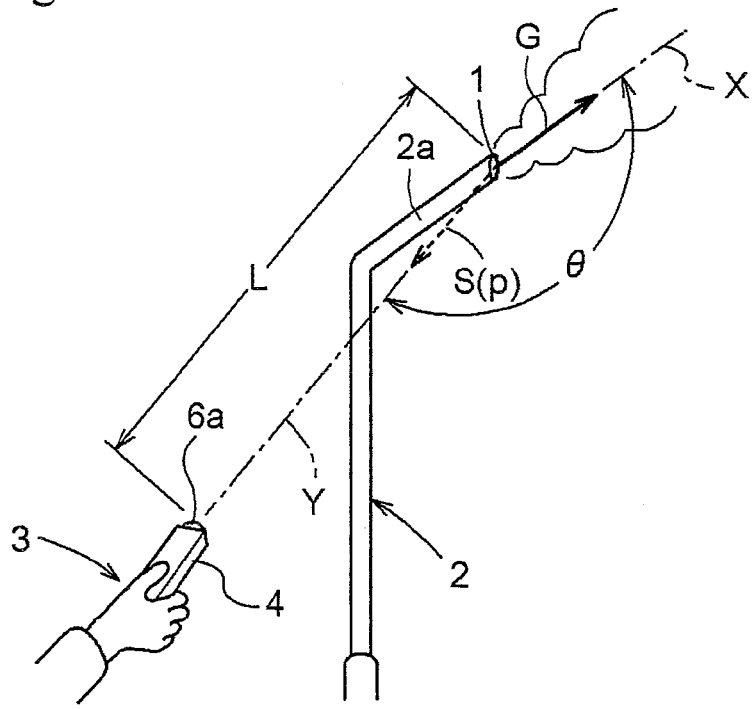
FIG. 1 is a perspective view showing a mode of implementing a discharge flow rate determination.

FIG. 1 shows a condition in which a discharge flow rate Q of a gas G (e.g. factory exhaust gas to be discharged into the atmosphere) discharged from a discharge opening 1 provided outdoors is being determined. The discharge opening 1 is formed at the leading end of a discharge pipe 2 (discharge passageway) installed vertically.

In order to prevent entrance of raindrops or water into the discharge pipe 2, an upper end portion 2a of the discharge pipe 2 is bent oblique. The discharge opening 1 is formed by cutting off the leading end of the discharge pipe upper end portion 2a along a pipe axis X such that its opening face may assume a substantially perpendicular posture and oriented toward the bending direction of the leading end of the discharge pipe upper end portion 2a.

Figure 2:
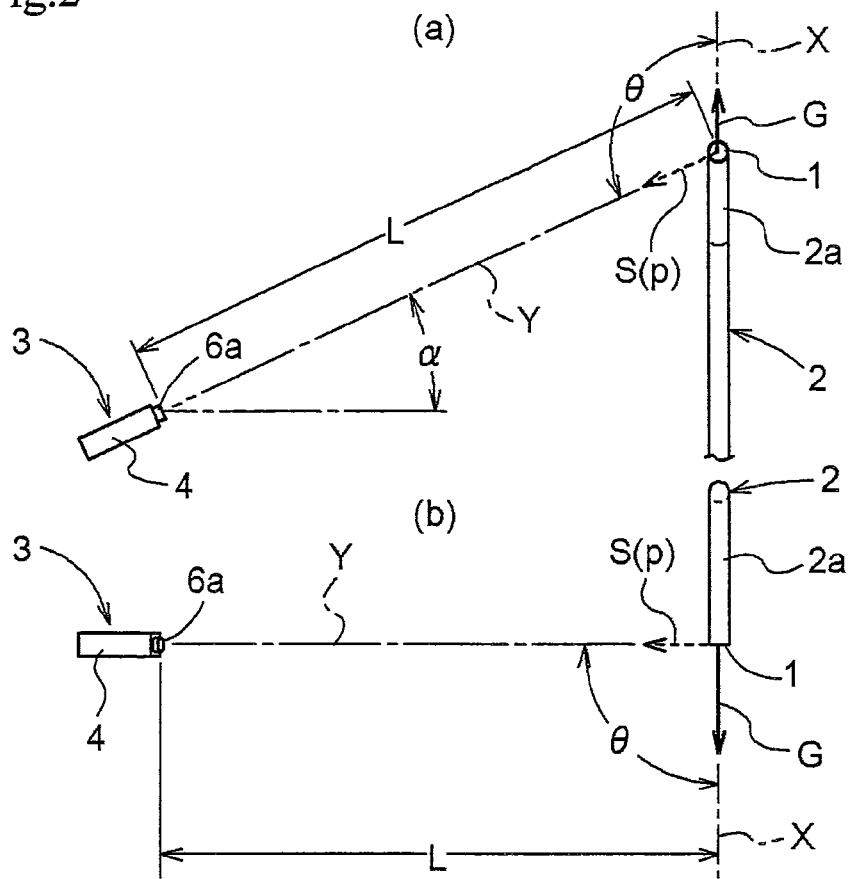
FIG. 2 are a schematic elevation view and a schematic plane view showing positional relationship of a determination site.

As the discharge opening 1 is located at a high position, determination of the discharge flow rate Q will be effected as the user looks up the discharge opening 1 as illustrated in FIG. 2 (a). In this example, as shown in FIG. 2 (b), the determining operation is made for a determination site 3 which is a lower position in the direction Y normal to a discharge direction X (i.e. the pipe axis direction of the bent discharge pipe upper end portion 2a) of gas from the discharge opening 1 in the plane view.

Figure 3:
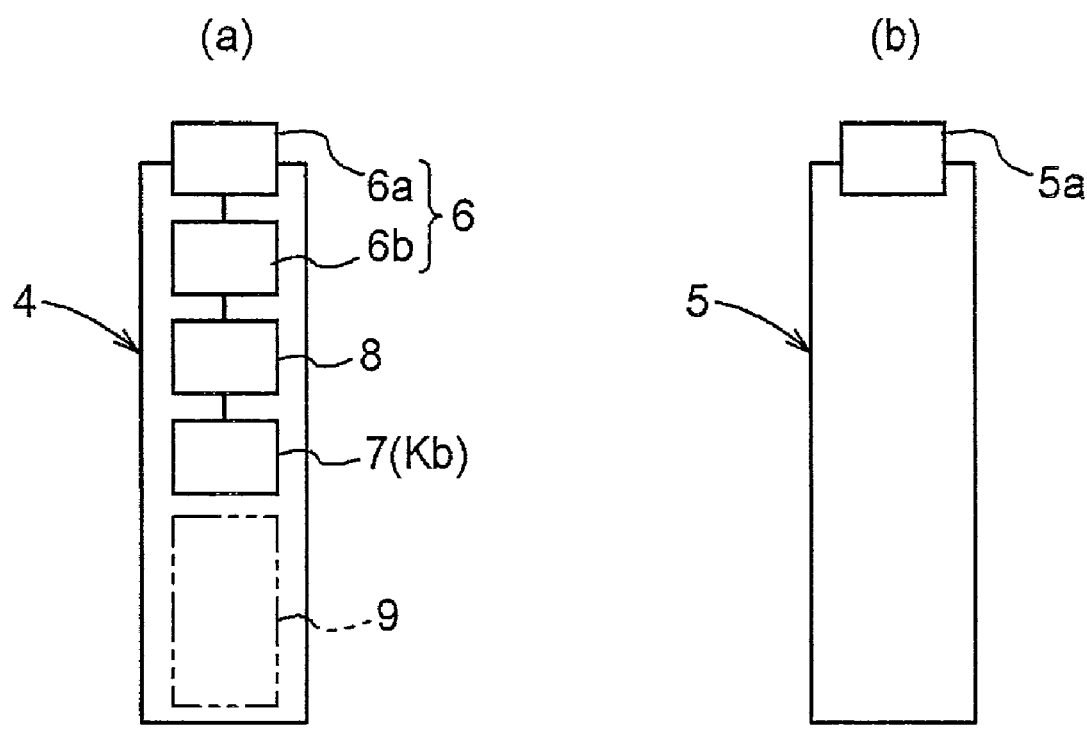
FIG. 3 is a plane view of a metering instrument and a distance meter.

The determination is made at the determination site 3 with using a portable metering instrument 4 and a portable distance meter 5. As shown in FIG. 3 (a), the metering instrument 4 includes a supersonic wave determining portion 6 for determining intensity (p) of a supersonic wave S (in other words, acoustic pressure) generated at and propagated from discharge opening 1 in association with discharge of gas from this discharge opening 1. This supersonic wave determining portion 6 consists essentially of a directional microphone 6a and a processor 6b for electrically processing supersonic wave reception signals of this microphone 6a.

The microphone 6a is disposed at the leading end of the metering instrument 4. The directional center axis of the microphone 6a is oriented to the front direction of the metering instrument 4.

The processor 6a digitizes the intensity (s) of the supersonic wave S received by the microphone 6a as a determination process of the supersonic wave intensity and causes this supersonic intensity (p) as the digitized determination result to be displayed on a display (not shown) of the metering instrument 4. Further, the processor 6a generates an audible sound according to the determined supersonic wave intensity (s) and outputs this to e.g. an earphone.

That is to say, in the determination of the intensity (s) of the propagated supersonic wave S from the discharge opening 1, at the determination site 3, with the microphone 6a being oriented substantially toward the discharge opening 1, the operator will check the intensity (p) of the received supersonic wave S from the displaying on the display and/or the earphone output, while the operator gradually changes the orientation of the metering instrument 4 (that is, the orientation of the directional center axis of the microphone 6a toward the discharge opening 1).

And, in the course of this orientation change, a particular orientation where the intensity (s) of the received supersonic wave S is strongest will be set as the orientation for determination and the intensity (s) of the received supersonic wave S at this particular orientation will be obtained as the determined intensity of the propagated supersonic wave.

The metering instrument 4 includes, in addition to the supersonic wave determining portion 6 and the display described above, a storing portion 7 for storing various kinds of information needed for determination, a calculating portion 6 for effecting various kinds of calculation and an operational section 9 for effecting various kinds of operation. The storing portion 7 stores therein in advance a correlation Kb existent among an intensity (p) of propagated supersonic wave S from the discharge opening 1, a propagation distance L from the discharge opening 1 to the determination site 3 and a gas discharge flow rate G from the discharge opening 1.

This correlation Kb is obtained experimentally and prepared in the form of mathematical form or a data table and stored as such in the storing section 7 of the metering instrument 4.

The distance meter 5 is used for determining the propagation distance L. As this distance meter 5, there is employed a distance meter 5 of e.g. laser type, configured to determine a distance to a target, with its metering end 5a provided at its leading end being directed to the target.

That is, at the determination site 3, the metering end 5a of the distance meter 5 will be directed toward the discharge opening 1 and under this condition, the distance to the discharge opening 1 is determined, whereby the propagation distance L is obtained. And, this determined propagation distance L will be inputted to the metering instrument 4 with an input operation by the operational portion 9 as the inputting portion of the metering instrument 4.

Referring to the calculating portion 8 of the metering instrument 4, after the propagation distance L is inputted to the metering instrument 4 and upon completion of the determination of the supersonic intensity (p) at the determination site 3, the calculating portion 8 will obtain the fluid discharge flow rate Q from the discharge opening 1 from the determined supersonic intensity (p) and the propagation distance L, based upon the correlation Kb existent among the intensity (p) of propagated supersonic wave S from the discharge opening 1 and the propagation distance L from the discharge opening 1 to the determination site 3 and the gas discharge flow rate G from the discharge opening 1 and then causing this calculated gas discharge flow rate Q to be displayed on the display of the metering instrument 4 as the outputting portion.

That is, according to the present embodiment described so far, the method for determining a flow rate of a fluid discharged from a discharge opening 1 formed at a terminal end of a discharge passageway 2, the method comprises the steps of:
determining intensity (p) of a supersonic wave S generated at and propagated from the discharge opening 1 in association with discharge of the fluid from the discharge opening 1, at a determination site 3 distant from the discharge opening 1;
determining or investigating the propagation distance L from the discharge opening 1 to the determination site 3;
determining the discharge flow rate Q of the fluid from the discharge opening 1 from the determined or investigated supersonic wave intensity (p) and the propagation distance L, based on a correlation Kb existent between the intensity (p) of the supersonic wave S at the determination site 3, the propagation distance L and the discharge flow rate Q of the fluid from the discharge opening 1.

In the above, if higher determination precision is required for the discharge flow rate determination, a correction relating to a propagation angle θ can be added to the gas discharge flow rate Q displayed as the determination result on the display of the metering instrument 4.

That is to say, the propagation angle θ formed by the propagation direction Y of the propagated supersonic wave S to the determination site 3 relative to the gas discharge direction X is determined or investigated and a correction according to this propagation angle θ is added to the gas discharge flow rate Q displayed on the display of the metering instrument 4 and this corrected gas discharge flow rate Q' (=Q×correction function f(θ)) will be provided as the final determination result.

Referring more particularly to this correction relating to the propagation angle θ, in this embodiment, as described above, the lower position in the direction normal to the gas discharge direction X (the pipe axis direction of the bent discharge pipe upper end portion 2a) from the discharge opening 1 is used as the determination site 3. Therefore, the propagation angle δ is obtained in the following manner.

At the time of the determination of the propagation distance L at the determination site 3, with the leading end metering end 5a of the distance meter 5 being directed toward the discharge opening 1, an elevation angle α of the metering end 5a of the distance meter 5 is determined as well.

Or, at the time of the determination of the intensity (s) of the supersonic wave S at the determination site, with the microphone 6a attached to the leading end of the metering instrument 4 being directed to the discharge opening 1, an elevation angle α of the microphone 6a is determined as well.

On the other hand, with reference to e.g. a piping system diagram, the discharge direction X of the gas G from the discharge opening 1 is investigated and based upon this investigated gas discharge direction X and the above-described determined elevation angle α (that is, corresponding to the supersonic wave propagation direction Y to the determination site 3), the propagation angle θ is obtained.

And, to the gas discharge flow rate Q displayed on the display of the metering instrument 4, this propagation angle θ is added for its correction and this corrected gas discharge flow rate Q' (=Q×correction factor f(θ)) will be provided as the final determination result.

In the above, there have been described the case wherein the gas discharge flow rate Q displayed as the determination result on the display of the metering instrument 4 is subjected to correction according to the propagation angle θ. Instead, a similar or equivalent function to this correction maybe included in the metering instrument 4.

That is to say, in the metering instrument 4, the correlation to be stored in the storing portion 7 is set as the correlation Kd existent among the intensity (p) of the supersonic wave S, the propagation distance L, the propagation angle θ and the fluid discharge flow rate Q from the discharge opening 1.

Further, the calculating portion 8 will be configured to calculate the gas discharge flow rate Q from the discharge opening 1, from the supersonic wave intensity (p) determined at the determination site 3 by the supersonic wave determining portion 6, the propagation distance L and the propagation angle θ that are inputted to the operating portion 9 as the inputting portion and based upon the correlation Kd stored at the storing portion 7.

That is to say, in either the method of separately effecting correction on the propagation angle θ or the method of providing the metering instrument 4 with the equivalent function, the method for determining a flow rate Q' of a fluid G discharged from a discharge opening 1 formed at a terminal end of a discharge passageway 2, the method comprising the steps of:
determining intensity (p) of a supersonic wave S generated at and propagated from the discharge opening 1 formed at the terminal end of the discharge passageway 2 in association with discharge of the fluid from the discharge opening, at a determination site 3 distant from the discharge opening 1;
determining or investigating a propagation distance L from the discharge opening 1 to the determination site 3 and a propagation angle θ formed by the propagation direction Y of the propagated supersonic wave S to the determination site 3 relative to the direction X of the fluid discharge from the discharge opening 1; and
determining the discharge flow rate Q' of the fluid from the discharge opening 1 from the determined supersonic wave intensity (p), the propagation distance L and the propagation angle θ, based on a correlation existent among the intensity of the supersonic wave S, the propagation distance L, the propagation angle θ and the flow rate Q of the fluid discharged from the discharge opening 1.

Figure 4:
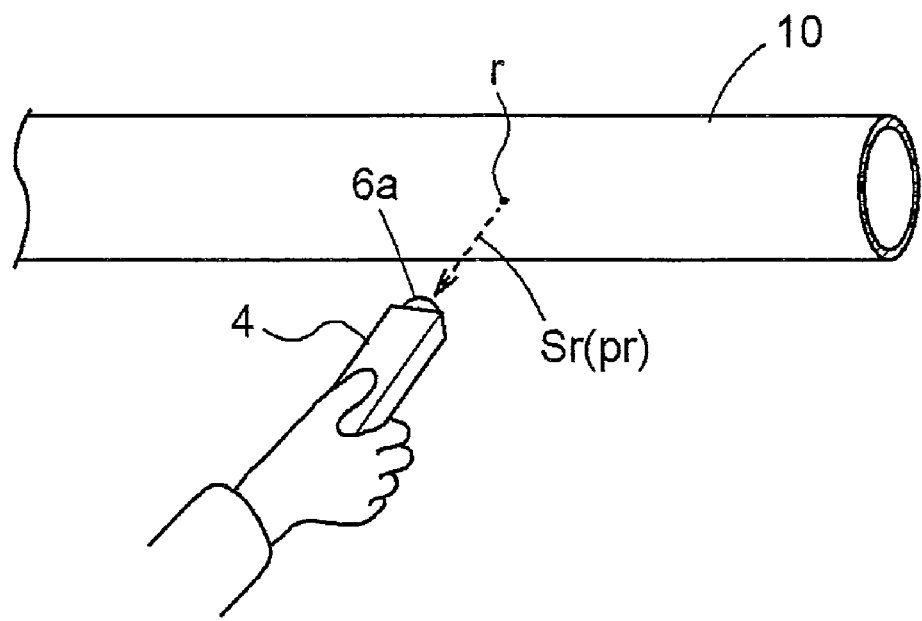
FIG. 4 is a perspective view showing implementations of a leaking portion search and a leakage flow rate determination.

The metering instrument 4 disclosed in this embodiment, with a necessary mode changing operation, can be used in, instead of its original use of the discharge flow rate determining mode, but in the leaking portion searching mode for searching a small fluid leaking portion (r) due to e.g. a pinhole generated at a pipe 10 or a tank or connection failure at a pipe joint as shown in FIG. 4 or in the leakage flow rate determining mode for determining a fluid leakage flow rate (q) at the leaking portion (r).

That is, in the leaking portion searching mode, the intensity (pr) of the generated supersonic wave Sr in association with occurrence of fluid leakage at the leaking portion (r) is determined by the supersonic wave determining portion 6, with the metering instrument 4 being gradually moved or change in posture so that the orientation of the microphone 6a of the metering instrument 4 is moved gradually along e.g. a pipe 10.

And, change in the determined supersonic intensity (pr) in association with this movement or change in posture is confirmed through intensity display on the display or an earphone output, and the determination may be made in such a mode that when the determined supersonic wave intensity (pr) is at maximum on the variation pattern of this determined supersonic wave intensity (pr), it is determined that there is high likelihood of presence of the leaking portion (r) at the terminal distal end of the orientation of the microphone 6a. In this way, the small leaking portion (r) present in a pipe 10 or a tank can be searched.

Further, in the leakage flow rate determining mode, the intensity (pr) of the generated supersonic wave Sr in association with occurrence of fluid leakage at the leaking portion (r) is determined by the supersonic wave determining portion 6, with the microphone 6a of the metering instrument 4 being oriented toward the leaking portion (r) in the pipe 10 or a tank.

Then, based on the correlation Kr stored in the storing portion 7 (that is, the correlation existent among the intensity (pr) of the leaking portion generated supersonic wave Sr and the leaking flow rat (q)), the calculating portion 8 will be caused to calculate the fluid leakage flow rate (q) at the leaking portion (r) from the determined supersonic wave intensity (pr) and this calculated fluid leakage flow rate (q) will be caused to be displayed on the display.

While the necessary mode change operation will differ, depending on the mode of embodiment of the mode selection, some non-limiting examples of operation include change in the determination sensitivity or determination frequency of the supersonic wave determining portion 6, change in the calculation program of the calculating portion 8, change in the information stored in the storing portion 7, change in a portion of the hardware of the apparatus.

[Other Embodiments]

Next, some other embodiments of the present invention will be described respectively.

In the foregoing embodiment, there was described the arrangement capable of flexibly coping with difference in the propagation distance L from the discharge opening 1 to the determination site 3, thus effecting determination, with the determination site not being restricted by the propagation distance L. However, in the case of a simplified discharge flow rate determining apparatus that effects determination on the assumption of the propagation distance L being fixed, the storing portion 7 and the calculating portion 8 of the metering instrument 4 can be modified as follows.

The storing portion 7 will be configured to store in advance a correlation Kc existent among the intensity (p) of the propagated supersonic wave S at the determination site 3, the propagation angle θ and the gas discharge flow rate Q from the discharge opening 1.

And, the calculating portion 8 will be configured to calculate the gas discharge flow rate Q from the discharge opening 1 from the supersonic wave intensity (p) of the propagated supersonic wave S at the determination site 3 and the propagation angle θ inputted to the inputting portion, based upon the correlation Kc stored at the storing portion 7 and to cause this calculated gas discharge flow rate Q as the determination result to be displayed on the display.

That is to say, in this case, the discharge flow rate determining method for determining a flow rate Q of fluid G discharge form a discharge opening 1 formed at a terminal end of a discharge passageway 2, comprises the steps of:

determining intensity (p) of a supersonic wave S generated at and propagated from the discharge opening 1 in association with discharge of the fluid from the discharge opening 1, at a determination site 3 distant from the discharge opening 1;

determining or investigating a propagation angle θ formed by the propagation direction Y of the propagated supersonic wave S to the determination site 3 relative to the direction X of the fluid discharge from the discharge opening 1; and determining the discharge flow rate Q of the fluid from the discharge opening 1 from the determined supersonic wave intensity (p) and the propagation angle θ, based on a correlation Kc existent among the intensity (p) of the supersonic wave S at the determination site 3, the propagation angle θ and the flow rate Q of the fluid discharged from the discharge opening 1.

Further, in the case of a simplified discharge flow rate determining apparatus, the storing portion 7 and the calculating portion 8 of the metering instrument 4 can be modified as follows.

The storing portion 7 will be configured to store in advance a correlation Ka existent between the intensity (p) of the propagated supersonic wave S at the determination site 3 and the gas discharge flow rate Q from the discharge opening 1.

And, the calculating portion 8 will be configured to calculate the gas discharge flow rate Q from the discharge opening 1 from the supersonic wave intensity (p) of the propagated supersonic wave S determined by the supersonic wave determining portion 6 at the determination site 3, based upon the correlation Ka stored at the storing portion 7 and to cause this calculated gas discharge flow rate Q as the determination result to be displayed on the display.

That is to say, in this case, the discharge flow rate determining method for determining a flow rate Q of fluid G discharge form a discharge opening 1 formed at a terminal end of a discharge passageway 2, comprises the steps of:

determining intensity (p) of a supersonic wave S generated at and propagated from the discharge opening 1 in association with discharge of the fluid from the discharge opening 1, at a determination site 3 distant from the discharge opening 1; and determining the discharge flow rate Q of the fluid from the discharge opening 1, based on a correlation Ka existent between the intensity (p) of the supersonic wave S at the determination site 3 and the flow rate Q of the fluid discharged from the discharge opening 1.

As to the apparatus configuration of the determining apparatus, the metering instrument 4 may be configured to include integrally a distance metering means for metering the propagation distance L. Or, the metering instrument 4 may be configured to include integrally angle metering means for metering the propagation angle θ and a reference angle for obtaining it.

Conversely, the supersonic wave determining portion 6 in the metering instrument 4 may be provided separately from the other portions of the same.

Further, it may be arranged such that the determining apparatuses according to the seventh through tenth characterizing features may be realized with mode switchover of a single discharge flow rate determining apparatus.

The discharge flow rate determining apparatus need not be configured to be capable of mode switchover to the leaking portion searching mode or the leakage flow rate determining mode. Instead, the apparatus may be dedicated to the use in the discharge flow rate determining mode for determining the fluid discharge flow rate from the discharge opening.

The supersonic wave determining portion 6, the storing portion 7, the calculating portion 8 and the display as an outputting portion disclosed in the foregoing embodiment correspond respectively to what are defined as the "supersonic wave determining means", "storing means", "calculating means" and "outputting means" in the characterizing features of the present invention.

INDUSTRIAL APPLICABILITY

The discharge flow rate determining method and the discharge flow rate determining apparatus according to the present invention may be used in various fields for determination of flow rates of various kinds of fluid discharged from a discharge opening.

DESCRIPTION OF REFERENCE MARKS 2 discharge passageway
1 discharge opening
G fluid
Q flow rate
3 determination site
S propagated supersonic wave
p supersonic wave intensity
L propagation distance
Y propagation direction
X fluid discharge direction
θ propagation angle
Ka-Kd correlations
6a microphone
5a metering end of distance meter
6 supersonic wave determining means
7 storing means
8 calculating means
9 inputting portion
r leaking portion
Sr leaking portion generated supersonic wave
pr supersonic wave intensity
q fluid leakage flow rate

The invention claimed is:

1. A method of using a discharge flow rate determining apparatus comprising:
supersonic wave determining means for determining intensity of a supersonic wave generated at and propagated from the discharge opening in association with discharge of the fluid from the discharge opening, at a determination site distant from the discharge opening;
storing means for storing a correlation existent between the intensity of the supersonic wave at the determination site and the discharge flow rate of the fluid from the discharge opening;
calculating means for calculating the discharge flow rate of the fluid from the discharge opening from the supersonic wave intensity determined by the supersonic wave determining means at the determination site, based on the correlation stored in the storing means; and
outputting means for outputting the discharge flow rate of the fluid from the discharge opening calculated by the calculating means as the determination result;
comprising the steps for configuring the apparatus to be capable of selectively providing;
a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and
a leaking portion searching mode in which intensity of the supersonic wave generated at a leaking portion in association with leakage of fluid is determined by the supersonic wave determining means while the supersonic wave determining means is being moved or changed in its posture and the leaking portion is searched based upon the determined intensity of the supersonic wave at the leaking portion; and
selectively effecting the discharge flow rate determining mode and the leaking portion searching mode.

2. A method of using a discharge flow rate determining apparatus comprising:
supersonic wave determining means for determining intensity of a supersonic wave generated at and propagated from the discharge opening in association with discharge of the fluid from the discharge opening, at a determination site distant from the discharge opening;
storing means for storing a correlation existent among the intensity of the supersonic wave, the propagation distance from the discharge opening to the determination site and the discharge flow rate of the fluid from the discharge opening;
calculating means for calculating the discharge flow rate of the fluid from the discharge opening from the supersonic wave intensity determined by the supersonic wave determining means at the determination site and the propagation distance inputted to an inputting section, based on the correlation stored in the storing means; and
outputting means for outputting the discharge flow rate of the fluid from the discharge opening calculated by the calculating means as the determination result;
comprising the steps for configuring the apparatus to be capable of selectively providing;
a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and
a leaking portion searching mode in which intensity of the supersonic wave generated at a leaking portion in association with leakage of fluid is determined by the supersonic wave determining means while the supersonic wave determining means is being moved or changed in its posture and the leaking portion is searched based upon the determined intensity of the supersonic wave at the leaking portion; and selectively effecting the discharge flow rate determining mode and the leaking portion searching mode.

3. A method of using a discharge flow rate determining apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent among the intensity of the propagated supersonic wave at the determination site, a propagation angle formed by the propagation direction of the propagated supersonic wave to the determination site relative to the direction of the fluid discharge from the discharge opening and the fluid discharge flow rate from the discharge opening;

calculating means for calculating the discharge flow rate of the fluid from the discharge opening from the supersonic wave intensity determined by the supersonic wave determining means at the determination site and the propagation angle inputted to an inputting section, based on the correlation stored in the storing means; and outputting means for outputting the discharge flow rate of the fluid from the discharge opening calculated by the calculating means as the determination result;

comprising the steps for configuring the apparatus to be capable of selectively providing;

a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and a leaking portion searching mode in which intensity of the supersonic wave generated at a leaking portion in association with leakage of fluid is determined by the supersonic wave determining means while the supersonic wave determining means is being moved or changed in its posture and the leaking portion is searched based upon the determined intensity of the supersonic wave at the leaking portion; and selectively effecting the discharge flow rate determining mode and the leaking portion searching mode.

4. A method of using a discharge flow rate determining apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent among the intensity of the supersonic wave at the determination site, the propagation distance from the discharge opening to the determination site, the propagation angle formed by the propagation direction of the propagated supersonic wave to the determination site relative to the direction of the fluid discharge from the discharge opening and the fluid discharge flow rate from the discharge opening;

calculating means for calculating the discharge flow rate of the fluid from the discharge opening from the supersonic wave intensity determined by the supersonic wave determining means, the propagation distance and the propagation angle inputted to an inputting section, based on the correlation stored in the storing means; and outputting means for outputting the discharge flow rate of the fluid from the discharge opening calculated by the calculating means as the determination result;

comprising the steps for configuring the apparatus to be capable of selectively providing;

a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and a leaking portion searching mode in which intensity of the supersonic wave generated at a leaking portion in association with leakage of fluid is determined by the supersonic wave determining means while the supersonic wave determining means is being moved or changed in its posture and the leaking portion is searched based upon the determined intensity of the supersonic wave at the leaking portion; and selectively effecting the discharge flow rate determining mode and the leaking portion searching mode.

5. A method of using a discharge flow rate determining apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent between the intensity of the supersonic wave at the determination site and the discharge flow rate of the fluid from the discharge opening;

calculating means for calculating the discharge flow rate of the fluid from the discharge opening from the supersonic wave intensity determined by the supersonic wave determining means at the determination site, based on the correlation stored in the storing means; and outputting means for outputting the discharge flow rate of the fluid from the discharge opening calculated by the calculating means as the determination result;

comprising the steps for configuring the apparatus to be capable of selectively providing;

a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and a leakage flow rate determining mode in which intensity of the supersonic wave generated at a leaking portion in association with leakage of fluid is determined by the supersonic wave determining means and the calculating means is caused to calculate a fluid leakage flow rate at the leaking portion based upon the determined intensity of the supersonic wave at the leaking portion; and selectively effecting the discharge flow rate determining mode and the leaking portion searching mode.

6. A method of using a discharge flow rate determining apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent among the intensity of the supersonic wave, the propagation distance from the discharge opening to the determination site and the discharge flow rate of the fluid from the discharge opening;

calculating means for calculating the discharge flow rate of the fluid from the discharge opening from the supersonic wave intensity determined by the supersonic wave determining means at the determination site and the propagation distance inputted to an inputting section, based on the correlation stored in the storing means; and outputting means for outputting the discharge flow rate of the fluid from the discharge opening calculated by the calculating means as the determination result;

comprising the steps for configuring the apparatus to be capable of selectively providing;

a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and a leakage flow rate determining mode in which intensity of the supersonic wave generated at a leaking portion in association with leakage of fluid is determined by the supersonic wave determining means and the calculating means is caused to calculate a fluid leakage flow rate at the leaking portion based upon the determined intensity of the supersonic wave at the leaking portion; and selectively effecting the discharge flow rate determining mode and the leaking portion searching mode.

7. A method of using a discharge flow rate determining apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent among the intensity of the supersonic wave, the propagation distance from the discharge opening to the determination site and the discharge flow rate of the fluid from the discharge opening;

calculating means for calculating the discharge flow rate of the fluid from the discharge opening from the supersonic wave intensity determined by the supersonic wave determining means at the determination site and the propagation distance inputted to an inputting section, based on the correlation stored in the storing means; and outputting means for outputting the discharge flow rate of the fluid from the discharge opening calculated by the calculating means as the determination result;

comprising the steps for configuring the apparatus to be capable of selectively providing;

a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and a leakage flow rate determining mode in which intensity of the supersonic wave generated at a leaking portion in association with leakage of fluid is determined by the supersonic wave determining means and the calculating means is caused to calculate a fluid leakage flow rate at the leaking portion based upon the determined intensity of the supersonic wave at the leaking portion; and selectively effecting the discharge flow rate determining mode and the leaking portion searching mode.

8. A method of using a discharge flow rate determining apparatus comprising:

supersonic wave determining means for determining intensity of a supersonic wave generated at and propagated from the discharge opening in association with discharge of the fluid from the discharge opening, at a determination site distant from the discharge opening;

storing means for storing a correlation existent among the intensity of the supersonic wave at the determination site, the propagation distance from the discharge opening to the determination site, the propagation angle formed by the propagation direction of the propagated supersonic wave to the determination site relative to the direction of the fluid discharge from the discharge opening and the fluid discharge flow rate from the discharge opening;

calculating means for calculating the discharge flow rate of the fluid from the discharge opening from the supersonic wave intensity determined by the supersonic wave determining means, the propagation distance and the propagation angle inputted to an inputting section, based on the correlation stored in the storing means; and outputting means for outputting the discharge flow rate of the fluid from the discharge opening calculated by the calculating means as the determination result;

comprising the steps for configuring the apparatus to be capable of selectively providing;

a discharge flow rate determining mode in which intensity of the supersonic wave generated at and propagated from the discharge opening in association with discharge of the fluid from the discharge opening is determined by the supersonic wave determining means and the calculating means is caused to calculate the discharge flow rate of the fluid from the discharge opening based upon the determined supersonic wave intensity, and a leakage flow rate determining mode in which intensity of the supersonic wave generated at a leaking portion in association with leakage of fluid is determined by the supersonic wave determining means and the calculating means is caused to calculate a fluid leakage flow rate at the leaking portion based upon the determined intensity of the supersonic wave at the leaking portion; and selectively effecting the discharge flow rate determining mode and the leaking portion searching mode.

9. A method for determining a flow rate of a fluid discharged from a discharge opening using a discharge flow rate determining apparatus, the apparatus comprising:

supersonic wave determining means for determining intensity of a supersonic wave generated at and propagated from the discharge opening in association with discharge of the fluid from the discharge opening, at a determination site distant from the discharge opening formed at a terminal end of a discharge passageway;

storing means for storing a correlation existent among the intensity of the propagated supersonic wave at the determination site, a propagation angle formed by the propagation direction of the propagated supersonic wave to the determination site relative to the direction of the fluid discharge from the discharge opening, and the fluid discharge flow rate from the discharge opening;

calculating means for calculation the discharge flow rate of the fluid from the discharge opening from the supersonic wave intensity determined by the supersonic wave determining means at the determination site and the propagation angle inputted to an inputting section, based on the correlation stored in the storing means; and outputting means for outputting the discharge flow rate of the fluid from the discharge opening calculated by the calculating means as the determination result, the method comprising the steps of:

determining the intensity of the supersonic wave at the determination site using a microphone as the supersonic wave determining means, the intensity of the supersonic wave being generated at and propagated from the discharge opening in associate with discharge of the fluid from the discharge opening;

placing the determination site, in a planar view, at a location present in the direction normal to the fluid discharge direction from the discharge opening;

investigating the discharge direction of the fluid from the discharge opening, and determining an elevation angle of the microphone at the determination site, the microphone being directed to the discharge opening; and obtaining the propagation angle based upon the investigated fluid discharge direction and the determined elevation angle.

10. A method for determining a flow rate of a fluid discharged from a discharge opening using a discharge flow rate determining apparatus, the apparatus comprising:

supersonic wave determining means for determining intensity of a supersonic wave generated at and propagated from the discharge opening in association with discharge of the fluid from the discharge opening, at a determination site distant from the discharge opening formed at a terminal end of a discharge passageway;

storing means for storing a correlation existent among the intensity of the propagated supersonic wave at the determination site, a propagation distance from the discharge opening to the determination site, a propagation angle formed by the propagation direction of the propagated supersonic wave to the determination site relative to the direction of the fluid discharge from the discharge opening, and the fluid discharge flow rate from the discharge opening;

calculating means for calculation the discharge flow rate of the fluid from the discharge opening from the supersonic wave intensity determined by the supersonic wave determining means at the determination site, and the propagation distance and the propagation angle inputted to an inputting section, based on the correlation stored in the storing means; and outputting means for outputting the discharge flow rate of the fluid from the discharge opening calculated by the calculating means as the determination result, the method comprising the steps of:

determining the intensity of the supersonic wave at the determination site using a microphone as the supersonic wave determining means, the intensity of the supersonic wave being generated at and propagated from the discharge opening in association with discharge of the fluid from the discharge opening;

placing the determination site, in a planar view, at a location present in the direction normal to the fluid discharge direction from the discharge opening;

determining or investigating the propagation distance from the discharge opening to the determination site;

investigating the discharge direction of the fluid from the discharge opening, and determining an elevation angle of the microphone at the determination site, the microphone being directed to the discharge opening, or determining an elevation angle of a distance meter at the determination site, the metering end of the distance meter being directed to the discharge opening, the distance meter configured to determine the distance to the discharge opening; and obtaining the propagation angle based upon the investigated fluid discharge direction and the determined elevation angle.

* * * * *